US006572886B2

(12) United States Patent
Ribadeau-Dumas et al.

(10) Patent No.: US 6,572,886 B2
(45) Date of Patent: Jun. 3, 2003

(54) DEXTROSE-BASED LOZENGES AND PROCESS FOR THEIR MANUFACTURE

(75) Inventors: Guillaume Ribadeau-Dumas, Verlinghem (FR); Véronique Beaudier, Lompret (FR)

(73) Assignee: Roquette Freres, Lestrem (FR)

( * ) Notice: Subject to any disclaimer, the term of this patent is extended or adjusted under 35 U.S.C. 154(b) by 38 days.

(21) Appl. No.: 09/761,103

(22) Filed: Jan. 16, 2001

(65) Prior Publication Data

US 2001/0009687 A1 Jul. 26, 2001

(30) Foreign Application Priority Data

Jan. 18, 2000 (FR) ............................................. 00 00588

(51) Int. Cl.⁷ ................................................. A61K 9/20
(52) U.S. Cl. ....................... 424/464; 424/439; 424/440; 424/441; 424/465
(58) Field of Search ................................ 424/439, 440, 424/441, 464, 465

(56) References Cited

U.S. PATENT DOCUMENTS

| 4,251,561 A | * 2/1981 | Gajewski ..................... 426/571 |
| 4,263,328 A | 4/1981 | Parada et al. |
| 4,614,207 A | 9/1986 | Steinhagen |
| 4,620,982 A | 11/1986 | Serpelloni |
| 4,882,156 A | 11/1989 | Yang et al. |
| 5,080,906 A | 1/1992 | Carenzi et al. |
| 5,409,905 A | 4/1995 | Eby, III |
| 5,614,207 A | 3/1997 | Shah et al. |
| 5,939,091 A | 8/1999 | Eoga et al. |

FOREIGN PATENT DOCUMENTS

| EP | 0 425 450 | 10/1990 |
| EP | 0 530 995 | 8/1992 |
| EP | 0 839 528 | 10/1996 |
| EP | 0 968 657 | 7/1999 |
| WO | 97/42941 | 5/1997 |

OTHER PUBLICATIONS

A. Slawatycki, Confectionery Production, Mar. 1971, pp 289–291.
R. Lees, E.B. Jackson "Sugar Confectionery and Chocolate Manufacture" pp 291–295 (1973).

* cited by examiner

*Primary Examiner*—James M. Spear
(74) *Attorney, Agent, or Firm*—Sturm & Fix LLP

(57) ABSTRACT

The invention relates to lozenges comprising a sweetening component and a binder, wherein more than 50% of the sweetening component consists of dextrose, this percentage being expressed by weight, based on the total weight of the sweetening component. The invention further relates to a process for the preparation of such lozenges.

8 Claims, No Drawings

DEXTROSE-BASED LOZENGES AND PROCESS FOR THEIR MANUFACTURE

FIELD OF THE INVENTION

The invention relates to lozenges in which the sweetening component consists predominantly of dextrose.

It further relates to a process for the manufacture of these lozenges.

BACKGROUND OF THE INVENTION

"Lozenges" are understood as meaning pastilles which are traditionally obtained from a paste based on finely ground sucrose. This paste, which contains a binder to assure adhesion between the sucrose crystals, is flavoured and optionally coloured and can also have pharmaceutical active principles added to it, after which it is converted to its definitive pastille form by rolling and then cutting, said pastilles being dried to remove the water which has necessarily been added in the preparation of the starting paste. The lozenges are therefore characteristically obtained without the need to apply a compressive force to the base starting material, as is the case for the preparation of tablets.

The lozenges must have a smooth surface and a homogeneous texture.

The intimate mixing between the liquid, especially the binding water, the pulverulent constituents, namely the sugar and the binder, and any other ingredients can be performed in a device of the kneader or extruder type.

The paste resulting from this mixing operation is converted to a layer of preselected thickness by rolling, and once the surface of the paste is sufficiently hard and dry to prevent any sticking to the cutting tools, the pastilles are cut to the desired shape before being dried. This cutting step is called stamping. As far as the hardening is concerned, this is generally effected by blowing with hot and/or cold air, optionally followed by dusting with e.g. starch or mannitol.

The drying is generally effected in controlled-atmosphere ovens in order to promote a uniform texture of the finished product, the drying temperatures generally being below 50° C. and the drying time less than 72 hours.

As far as the sweetening component is concerned, this generally consists of sucrose mixed with small amounts of glucose syrup or dextrose, and sometimes sorbitol or glycerol as humectants for slowing down the drying to give a regular surface.

"Sugar-free" lozenges exist in which the glucose syrups, sucrose and dextrose have been replaced with polyols such as xylitol, mannitol and hydrogenated starch hydrolyzates.

Patent EP 530 995, describing lozenges in which the sweetening component consists solely of maltitol or erythritol, may be cited in particular.

Another proposed way of obtaining "sugar-free" lozenges is to replace the sucrose with sorbitol (Confectionery Production, May 1971, pp. 289–291).

Lozenges based on crystallized fructose or sorbitol have also been proposed by the Assignee in patent U.S. Pat. No. 4,620,982.

The sugar-based lozenges are most often formulated with sucrose of very fine particle size, such as icing sugar. The addition of small amounts of glucose syrup improves the fineness of the paste but slows down the drying thereof. It is also possible to add small amounts of dextrose, which, when used as a very fine powder, has the advantage of giving the lozenge a refreshing effect; this is of particular value when mint flavourings are used in the lozenges (LEES R., JACKSON E. B., Sugar Confectionery and Chocolate Manufacture, pp. 29–295, 1973).

For economic reasons, attempts were then made to replace the sucrose with dextrose in lozenge formulations. However, dextrose can only be substituted for sucrose to the extent of about 50%. In fact, when the dextrose content of the sweetening component of the lozenge exceeds about 50% by weight, it is not possible to obtain as smooth a surface as that obtained with a sweetening component containing 100% of sucrose. The paste is very soft and sticky during kneading, so the rolling and stamping are more difficult. The lozenges are also very crumbly. Dextrose could therefore satisfactorily be substituted for sucrose only to the extent of about one third.

In the subsequent search to develop lozenges in which the sweetening component contains predominantly dextrose, the inventors have succeeded, after numerous experiments, in finding that it is possible, contrary to all expectation, to produce such lozenges which are as smooth as the lozenges containing predominantly sucrose and are of comparable hardness.

DESCRIPTION OF THE INVENTION

The invention therefore relates to lozenges comprising a sweetening component and a binder, characterized in that more than 50% of the sweetening component consists of dextrose, this percentage being expressed by weight, based on the total weight of the sweetening component.

The dextrose content of said sweetening component is preferably greater than 60%, particularly preferably greater than 75% and very particularly preferably greater than 90%, these percentages being expressed by weight, based on the total weight of the sweetening component. Among the suitable grades of dextrose, dextrose monohydrate, and especially ROFEROSE® SF marketed by the Assignee, may be mentioned in particular. The remainder to 100% advantageously consists of sucrose.

As regards the proportion of sweetening component, this preferably represents at least 80% by weight of the total weight of the lozenge.

The binder can consist of natural gums such as gum arabic or gum tragacanth, gelatin, starch or mixtures thereof. The binder is advantageously used in an amount of 0.5 to 8% by weight, based on the total weight of the lozenge.

The lozenges according to the invention are preferably prepared using an aqueous solution of gelatin.

As regards the water content of the lozenges according to the invention after drying, this is advantageously greater than or equal to 5% and preferably greater than or equal to 7% by weight, based on the total weight of the lozenge. Such water contents are unexpected as the traditional sucrose lozenges have water contents of the order of 1%. This is furthermore a definite economic advantage for the confectioners. Surprisingly, the lozenges according to the invention are totally satisfactory in terms of their hardness and their surface condition.

The lozenges according to the invention are obtainable by a process comprising the following steps: mixing of the pulverulent sweetening component with at least one binder in solution, kneading, rolling, stamping of the resulting paste to produce lozenges, and drying of the lozenges obtained, said process being characterized in that the binder is introduced in several portions into the sweetening component.

The pulverulent sweetening component is introduced into a kneader, which may or may not be heated. A suitable kneader is a mixer with zig-zag paddles. The binder in solution is then added to the sweetening component. The inventors have found, surprisingly and unexpectedly, that adding the binder in several portions is a neat way of giving the lozenges according to the invention their excellent surface condition. The binder is advantageously added in two portions. As for the preparation of sucrose lozenges, the paste can have flavourings, pharmaceutical active principles, colours and optionally acids added to it. The whole is intimately mixed and the paste is then rolled, stamped and dried in an oven at 30–50° C. for 8 to 24 hours to give lozenges whose quality is totally comparable to that of sucrose lozenges.

The advantages of the present invention will be understood more clearly from the Example which follows.

EXAMPLE 1

Preparation of Lozenges According to the Invention

| Formulation: | |
|---|---|
| ROFEROSE ® SF (dextrose monohydrate) by weight | 83% |
| Type A gelatin solution by weight 180 blooms at 10% solids content | 17% |

The dextrose monohydrate is introduced into an unheated kneader with zig-zag paddles.

Half of the gelatin solution is added and the mixture is kneaded for 6 minutes.

The other half of the gelatin solution is added and the mixture is kneaded for a further 6 minutes. The paste is then rolled to a thickness of 8 millimeters.

This paste is stamped and then dried for 24 hours at 20° C. and 50% relative humidity.

This gives lozenges containing 88.9% by weight of sweetening component (dextrose), 2% by weight of binder (gelatin) and 9.1% by weight of water. 100% of the sweetening component consists of dextrose.

These lozenges are as white, as smooth and as hard as lozenges containing predominantly sucrose.

What is claimed is:

1. A process for the preparation of a lozenge comprising a sweetening component and a binder and wherein more than 50% of the sweetening component consists of dextrose, this percentage being expressed by weight, based on the total weight of the sweetening component, comprising the following steps:

mixing of the sweetening component with at least one binder introduced in several portions into the sweetening component, kneading, rolling, stamping to produce lozenges, drying of the lozenges obtained.

2. A process according to claim 1, wherein the dextrose content of the sweetening component is greater than 60%, these percentage being expressed by weight, based on the total weight of the sweetening component.

3. A process according to claim 1, wherein the dextrose content of the sweetening component is greater than 75%, these percentage being expressed by weight, based on the total weight of the sweetening component.

4. A process according to claim 1, wherein the dextrose content of the sweetening component is greater than 90%, these percentage being expressed by weight, based on the total weight of the sweetening component.

5. A process according to claim 1, wherein the sweetener component represents at least 80% by weight of the total weight of the lozenges.

6. A process according to claim 1, wherein the binder represents 0.5% to 8% by weight of the total weight of the finished product.

7. A process according to claim 1, wherein the lozenge has a water content greater than or equal to 7% by weight.

8. A process according to claim 1, wherein 100% of the sweetening component consists of dextrose.

* * * * *